United States Patent [19]

Slough et al.

[11] 4,415,859

[45] Nov. 15, 1983

[54] PARAFFIN MONITOR

[75] Inventors: Carlton M. Slough, Spring; Edwin L. Colling, Jr., Sugarland, both of Tex.

[73] Assignee: Texaco Inc., White Plains, N.Y.

[21] Appl. No.: 371,358

[22] Filed: Apr. 23, 1982

Related U.S. Application Data

[63] Continuation-in-part of Ser. No. 194,697, Oct. 6, 1980, abandoned.

[51] Int. Cl.³ .................... G01N 27/00; G01N 33/28
[52] U.S. Cl. ............................. 324/442; 324/65 R; 324/204; 324/236; 422/68; 422/119; 436/141; 436/149
[58] Field of Search ............... 324/236, 204, 442, 239, 324/445, 65 CR, 446, 439, 61 QL, 65 R; 422/68, 119; 23/230 M, 230 HC; 331/65; 436/141, 149

[56] References Cited

U.S. PATENT DOCUMENTS

| | | | |
|---|---|---|---|
| 2,836,792 | 5/1958 | Weber | 324/65 R |
| 3,202,909 | 8/1965 | Stewart | 324/329 |
| 3,315,155 | 4/1967 | Colani | 324/239 |
| 3,635,681 | 1/1972 | Rogers | 422/68 |
| 3,746,975 | 7/1973 | Maltby | 324/65 R |
| 3,757,210 | 9/1973 | Hansen et al. | 324/65 CR |
| 3,840,806 | 10/1974 | Stoner et al. | 324/65 R |
| 4,183,029 | 1/1980 | Isayama et al. | 324/65 R |
| 4,220,916 | 9/1980 | Zimmermann et al. | 324/446 X |
| 4,266,187 | 5/1981 | Slough | 324/442 |
| 4,267,508 | 5/1981 | Ando | 324/236 X |
| 4,323,847 | 4/1982 | Karbowski | 331/65 X |

Primary Examiner—Kenneth M. Schor
Attorney, Agent, or Firm—Carl G. Ries; Robert A. Kulason; Ronald G. Gillespie

[57] ABSTRACT

A paraffin monitor includes a pair of probes which are immersed in a medium having paraffin contained therein. A circuit is connected to the probes which provides an output voltage. The characteristics of the electric circuit changes over a period of time, causing a corresponding change in the voltage output, in accordance with a change in the amount of paraffin on the probes.

8 Claims, 2 Drawing Figures

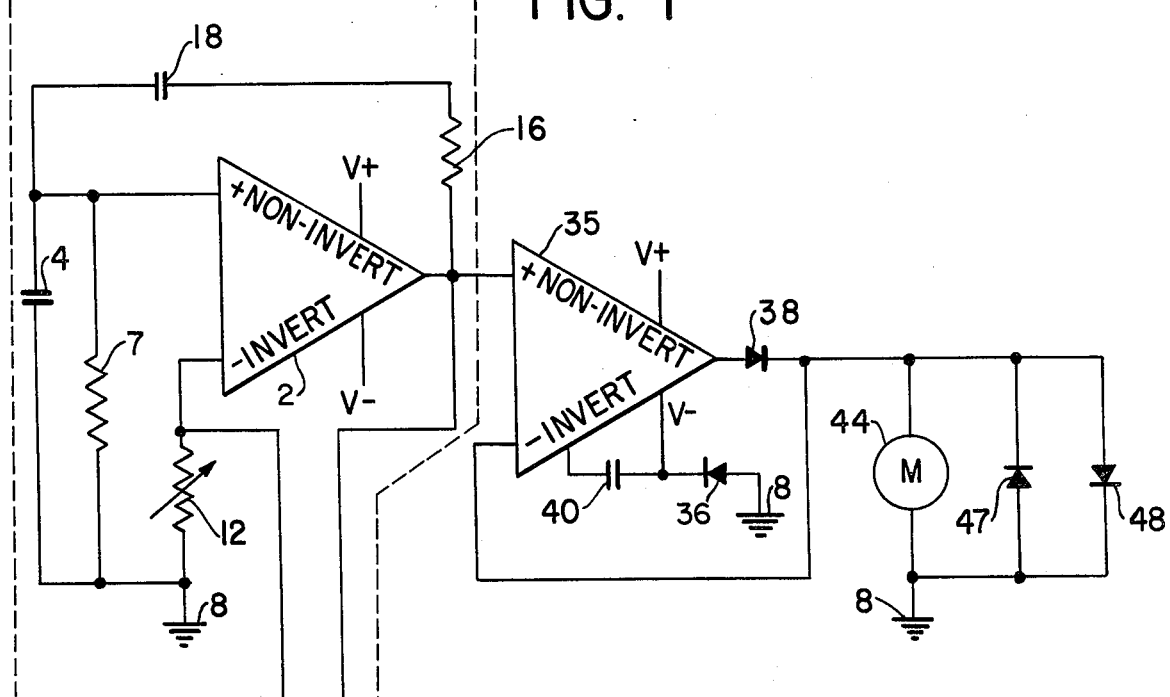
FIG. 1
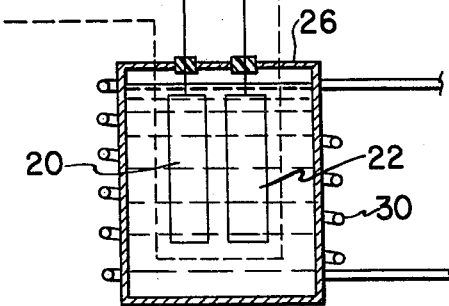
FIG. 2
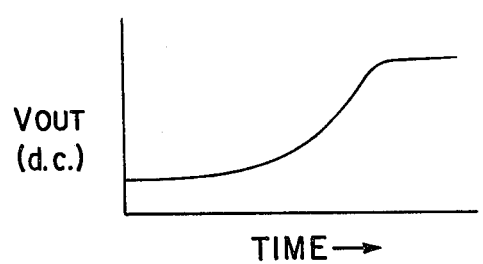

PARAFFIN MONITOR

CROSS REFERENCE TO RELATED APPLICATIONS

This application is a continuation as to all subject matter common to U.S. application Ser. No. 194,697 now abandoned and filed Oct. 6, 1980 by Carlton M. Slough and Edwin L. Colling, Jr. and assigned to Texaco Inc., assignee of the present invention, and a continuation-in-part for additional subject matter.

BACKGROUND OF THE INVENTION

Field of the Invention

The present invention relates to monitors in general and, more particularly, to monitors for monitoring characteristics of oils.

SUMMARY OF THE INVENTION

A paraffin monitor includes an electronic circuit providing an output voltage which is affected by a pair of probes, immersed in a medium having paraffin, that are part of the circuit so that over a period of time the voltage is representative of a change in the amount of paraffin on the probes.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE DRAWINGS

FIG. 1 is a schematic diagram of a paraffin monitor constructed in accordance with the present invention.

FIG. 2 is a graph showing the voltage reading on the meter shown in FIG. 1 versus time.

DESCRIPTION OF THE INVENTION

A need exists for a reliable method which can be used to monitor paraffin build-up over a period of time or to screen paraffin inhibitors and dispersants for crude oil prior to actual field use. A need also exists to be able to monitor paraffin build-up or dispersal in pipelines carrying crude oil production streams. The present invention is a paraffin monitor and may be used for the paraffin build-up directly or by monitoring the effect of an inhibitor or dispersant on the paraffin so as to test the inhibitor or dispersant.

For the purpose of the present invention the word "medium" will be used to denote a liquid containing some crude oil or to a liquid that is substantially, if not 100%, crude oil. The crude oil contains paraffin.

Referring to FIG. 1, an amplifier/oscillator 1 includes an operational amplifier 2 having a capacitor 4 shunted by a resistor 7 connected to its non-inverting input. Capacitor 4 and resistor 7 are also connected to ground 8 so as to form a parallel resistor-capacitor circuit. The inverting input of amplifier 2 has a variable resistor 12 connected to ground 8.

One feedback loop connecting an output of amplifier 2 to the non-inverting input of amplifier 2 includes a resistor 16 and a capacitor 18 connected in series. Probes 20, 22 are connected to the inverting input and the output, respectively, of amplifier 2 and with the medium between them form another feedback loop. Probes 20, 22 are located in a shaker 26 having a heater coil 30 wrapped around it.

Amplifier 2 experiences both positive and negative feedback and thus causes amplifier/oscillator 1 to function as amplifier and as an oscillator. The positive feedback is applied to resistors 7, 16 and capacitors 4, 18 which are arranged in a series-parallel configuration and in the absence of other consideration would provide a controlled audio oscillator which is very stable in frequency. The frequency f of operation being given by $f = 1/(2\pi\sqrt{R_T R_F C_T C_F})$ where $R_T C_T$ are the resistance and capacitance, respectively, of the parallel resistor-capacitor which in this example are provided by resistor 7 and capacitor 4, respectively. The terms $R_F C_F$ refer to the feedback resistance and capacitance, respectively, which are provided by resistor 16 and capacitor 18. When $R_T$ equals $R_F$ and $C_T$ equals $C_F$, the foregoing equation may be rewritten as $f = 1/(2\pi RC)$ where R is the resistance of resistor 7 or 16 and C is the capacitance of capacitor 4 or 18. The oscillator portion of amplifier/oscillator 1 provides a small AC current or voltage which prevents polarization of the paraffin. A DC current or voltage produces polarization effects of the paraffin in oil producing systems which either invalidates or complicates data interpretation.

The negative feedback amplifier function of amplifier/oscillator 1 is achieved through resistor 12 and the resistance between probes 20, 22. The gain of the amplifier function is the ratio of the resistance between probes 20, 22 to the resistance of potentiometer 12. Thus as paraffin is deposited on probes 20, 22, the negative feedback resistance increases causing an increase in the amplifier's function gain. Obviously, if paraffin is removed from probes 20 and 22, the gain of the amplifier function would decrease.

Another effect of paraffin build-up or growth on probes 20, 22 is to turn the oscillator function of elements 1, 4, 7, 12, 16 and 18 from controlled oscillations into uncontrolled oscillations due to the increase of positive feedback, the benefit of which will be explained hereinafter. The removal of paraffin causes the AC signal to go from uncontrolled oscillation, if there was sufficient paraffin on probes 20 and 22, to controlled oscillation.

The output of amplifier/oscillator 1 is provided to the non-inverting input of another operational amplifier 35. The output signal from amplifier 35 is provided to a diode 38 whose output is connected to the inverting input of amplifier 35. Amplifier 35 is connected to ground 8 through a diode 36. A capacitor 40 is also connected to diode 36 and amplifier 35.

The output of diode 38 is also connected to a meter 34 and diodes 47 and 48 which provide overvoltage protection for meter 44. Meter 44 and diodes 47, 48 are connected to ground 8. Meter 44 may be calibrated so that a normal high gain signal from diode 38 causes a reading on meter 44 that is approximately three-fourths of full scale. When the aforementioned uncontrolled oscillations occur, meter 44 will be driven to full scale as an indication of the severity of paraffin build-up on probes 20, 22.

Operational amplifiers 2 and 35 receive biasing voltages V+ and V− from a power supply not shown for convenience of explanation.

Formation and growth of a paraffin film on the probes 20, 22 change the loop characteristics and, in turn, change the Q and the gain of the present invention.

Referring to FIG. 2, which depicts the reading on voltmeter 44 versus time, a build-up of paraffin results in the output voltage increasing. When the paraffin build-up is severe, meter 44 reads full-scale due to the uncontrolled oscillation as noted previously.

The voltage provided to meter 44 may be related to the paraffin inhibitor or dispersant effectiveness. When a paraffin inhibitor is being tested, the lack of paraffin build-up or the increase in the build-up time is indicative of the inhibitor's efficiency. When a paraffin dispersant is being tested, the removal time of the paraffin, and the extent of removal, from probes 20, 22 are representative of the paraffin dispersant's effectiveness.

The present invention as hereinbefore described is a paraffin monitor. The present invention may also be used to test paraffin inhibitors and dispersants. The monitor includes a circuit, that functions as an amplifier and an oscillator providing a signal having controlled oscillation or uncontrolled oscillation, which is affected to alter the gain of the amplifier function and the type of oscillation of the signal.

What is claimed is:

1. A paraffin monitor which comprises:
    amplifier/oscillator means connected to ground, including a pair of probes immersed in a medium containing paraffin, the amplifier/oscillator means being means for providing an output signal corresponding to the quantity of paraffin on the probes while introducing a small anti-polarizing current in the medium between the probes; and
    indicating means connected to ground and to the amplifier/oscillator means, the indicating means being means for providing an indication of the change in the amount of paraffin on the probes in accordance with the output signal from the amplifier/oscillator means.

2. A monitor as described in claim 1 in which the amplifier/oscillator means includes:
    a first operational amplifier;
    a resistor connecting one input of the first operational amplifier to ground; and
    a first feedback loop including one input and the output of the first operational amplifier, the probes and the medium between the probes for affecting the gain of the first operational amplifier by the change of the amount of paraffin on the probe so as to detect the output signal.

3. A monitor as described in claim 2 in which the amplifier/oscillator means includes a parallel resistor-capacitor circuit connecting another input of the first operational amplifier to ground, and
    a second feedback loop including resistor and a capacitor connected in series between the output and the second input.

4. A monitor as described in claim 3 in which the first operational amplifier provides a signal having controlled oscillation until there is a sufficient increase in paraffin on the probes which causes the signal from the first operational amplifier to have uncontrolled oscillation.

5. A monitor as described in claim 4 in which the amplifier/oscillator means includes a second amplifier stage connecting the first operational amplifier to the indicating means which amplifies the signal from the first operational amplifier to provide the output signal to the indicating means.

6. A monitor as described in claim 5 in which the resistor in the parallel resistor-capacitor circuit and the resistor in the second feedback loop have the same resistance, and the capacitor in the parallel resistor-capacitor circuit has the same capacitance as the capacitor in the second feedback loop.

7. A monitor as described in claim 6 in which the indicating means is a meter.

8. A monitor as described in claim 7 further comprising:
    container means for containing the oil, and
    heater means for maintaining the oil at a predetermined temperature.

* * * * *